(12) United States Patent
Schmidt et al.

(10) Patent No.: US 9,289,154 B2
(45) Date of Patent: Mar. 22, 2016

(54) TECHNIQUES FOR TEMPERATURE MEASUREMENT AND CORRECTIONS IN LONG-TERM MAGNETIC RESONANCE THERMOMETRY

(75) Inventors: Rita Schmidt, Givataim (IL); Hadas Ziso, Kiryat Tivon (IL); Benny Assif, Ramat HaSharon (IL); Osnat Dogadkin, Tel Aviv-Jaffa (IL); David Freundlich, Haifa (IL); Yoav Levy, Hinanit (IL); Shuki Vitek, Haifa (IL)

(73) Assignee: InSightec Ltd., Tirat Carmel (IL)

( * ) Notice: Subject to any disclaimer, the term of this patent is extended or adjusted under 35 U.S.C. 154(b) by 1158 days.

(21) Appl. No.: 12/543,951

(22) Filed: Aug. 19, 2009

(65) Prior Publication Data

US 2011/0046472 A1 Feb. 24, 2011

(51) Int. Cl.
*A61B 5/055* (2006.01)
*G01R 33/48* (2006.01)
*A61N 7/00* (2006.01)
*G01R 33/565* (2006.01)

(52) U.S. Cl.
CPC ............ *A61B 5/055* (2013.01); *G01R 33/4804* (2013.01); *A61N 2007/0004* (2013.01); *G01R 33/56509* (2013.01); *G01R 33/56563* (2013.01)

(58) Field of Classification Search
CPC .................... G01R 33/4804; G01R 33/56563; G01R 33/56509; A61B 5/055
USPC .................................. 600/411–412; 601/2–4
See application file for complete search history.

(56) References Cited

U.S. PATENT DOCUMENTS

| | | |
|---|---|---|
| 2,795,709 A | 6/1957 | Camp |
| 3,142,035 A | 7/1964 | Harris |
| 3,942,150 A | 3/1976 | Booth et al. |
| 3,974,475 A | 8/1976 | Burckhardt et al. |
| 3,992,693 A | 11/1976 | Martin et al. |
| 4,000,493 A | 12/1976 | Spaulding et al. |
| 4,339,952 A | 7/1982 | Foster |
| 4,454,597 A | 6/1984 | Sullivan |
| 4,478,083 A | 10/1984 | Hassler et al. |
| 4,505,156 A | 3/1985 | Questo |
| 4,526,168 A | 7/1985 | Hassler et al. |

(Continued)

FOREIGN PATENT DOCUMENTS

| | | |
|---|---|---|
| DE | 4345308 C2 | 2/2001 |
| EP | 0560397 | 9/1993 |

(Continued)

OTHER PUBLICATIONS

Grimault, S. et al, Quantitative measurement of temperature by proton resonance frequency shift at low field: a general method to correct non-linear spatial and temporal phase deformations, Journal of Magnetic Resonance, 170, (2004) pp. 79-87.*

(Continued)

*Primary Examiner* — Ruth S Smith
(74) *Attorney, Agent, or Firm* — Morgan, Lewis & Bockius LLP

(57) ABSTRACT

Techniques for temperature measurement and correction in long-term MR thermometry utilize a known temperature distribution in an MR imaging area as a baseline for absolute temperature measurement. Phase shifts that arise from magnetic field drifts are detected in one or more portions of the MR imaging area, facilitating correction of temperature measurements in an area of interest.

24 Claims, 7 Drawing Sheets

(56) References Cited

U.S. PATENT DOCUMENTS

| | | |
|---|---|---|
| 4,537,074 A | 8/1985 | Dietz |
| 4,549,533 A | 10/1985 | Cain et al. |
| 4,554,925 A | 11/1985 | Young |
| 4,558,279 A | 12/1985 | Ackerman et al. |
| 4,858,597 A | 8/1989 | Kurtze et al. |
| 4,865,042 A | 9/1989 | Umemura et al. |
| 4,888,746 A | 12/1989 | Wurster et al. |
| 4,889,122 A | 12/1989 | Watmough et al. |
| 4,893,284 A | 1/1990 | Magrane |
| 4,937,767 A | 6/1990 | Reuschel et al. |
| 5,187,439 A | 2/1993 | Jensen et al. |
| 5,209,221 A | 5/1993 | Riedlinger |
| 5,247,935 A | 9/1993 | Cline et al. |
| 5,271,400 A | 12/1993 | Dumoulin et al. |
| 5,275,165 A | 1/1994 | Ettinger et al. |
| 5,284,144 A | 2/1994 | Delannoy et al. |
| 5,291,890 A | 3/1994 | Cline et al. |
| 5,307,812 A | 5/1994 | Hardy et al. |
| 5,307,816 A | 5/1994 | Hashimoto et al. |
| 5,318,025 A | 6/1994 | Dumoulin et al. |
| 5,323,779 A | 6/1994 | Hardy et al. |
| 5,327,884 A | 7/1994 | Hardy et al. |
| 5,329,930 A | 7/1994 | Thomas, III et al. |
| 5,368,031 A | 11/1994 | Cline et al. |
| 5,368,032 A | 11/1994 | Cline et al. |
| 5,378,987 A | 1/1995 | Ishihara et al. |
| 5,379,642 A | 1/1995 | Reckwerdt et al. |
| 5,391,140 A | 2/1995 | Schaetzle et al. |
| 5,413,550 A | 5/1995 | Castel |
| 5,443,068 A | 8/1995 | Cline et al. |
| 5,474,071 A | 12/1995 | Chapelon et al. |
| 5,485,839 A | 1/1996 | Aida et al. |
| 5,490,840 A | 2/1996 | Uzgiris et al. |
| 5,492,122 A | 2/1996 | Button et al. |
| 5,507,790 A | 4/1996 | Weiss |
| 5,520,188 A | 5/1996 | Hennige et al. |
| 5,526,814 A | 6/1996 | Cline et al. |
| 5,549,638 A | 8/1996 | Burdette |
| 5,553,618 A | 9/1996 | Suzuki et al. |
| 5,573,497 A | 11/1996 | Chapelon |
| 5,582,578 A | 12/1996 | Zhong et al. |
| 5,590,653 A | 1/1997 | Aida et al. |
| 5,590,657 A | 1/1997 | Cain et al. |
| 5,594,336 A | 1/1997 | Gullapalli et al. |
| 5,601,526 A | 2/1997 | Chapelon et al. |
| 5,605,154 A | 2/1997 | Ries et al. |
| 5,617,371 A | 4/1997 | Williams |
| 5,617,857 A | 4/1997 | Chader et al. |
| 5,633,586 A | 5/1997 | Finn |
| 5,643,179 A | 7/1997 | Fujimoto |
| 5,662,170 A | 9/1997 | Donovan et al. |
| 5,665,054 A | 9/1997 | Dory |
| 5,666,954 A | 9/1997 | Chapelon et al. |
| 5,676,673 A | 10/1997 | Ferre et al. |
| 5,687,729 A | 11/1997 | Schaetzle |
| 5,694,936 A | 12/1997 | Fujimoto et al. |
| 5,711,300 A | 1/1998 | Schneider et al. |
| 5,722,411 A | 3/1998 | Suzuki et al. |
| 5,739,625 A | 4/1998 | Falcus |
| 5,743,863 A | 4/1998 | Chapelon |
| 5,752,515 A | 5/1998 | Jolesz et al. |
| 5,759,162 A | 6/1998 | Oppelt et al. |
| 5,769,790 A | 6/1998 | Watkins et al. |
| 5,810,008 A | 9/1998 | Dekel et al. |
| 5,873,845 A | 2/1999 | Cline et al. |
| 5,897,495 A | 4/1999 | Aida et al. |
| 5,916,161 A | 6/1999 | Ishihara et al. |
| 5,938,600 A | 8/1999 | Van Vaals et al. |
| 5,938,608 A | 8/1999 | Bieger et al. |
| 5,947,900 A | 9/1999 | Derbyshire et al. |
| 5,984,881 A | 11/1999 | Ishibashi et al. |
| 6,004,269 A | 12/1999 | Crowley et al. |
| 6,023,636 A | 2/2000 | Wendt et al. |
| 6,042,556 A | 3/2000 | Beach et al. |
| 6,064,206 A | 5/2000 | Van Vaals et al. |
| 6,067,371 A | 5/2000 | Gouge et al. |
| 6,071,239 A | 6/2000 | Cribbs et al. |
| 6,113,559 A | 9/2000 | Klopotek |
| 6,128,522 A | 10/2000 | Acker et al. |
| 6,128,958 A | 10/2000 | Cain |
| 6,193,659 B1 | 2/2001 | Ramamurthy et al. |
| 6,194,899 B1 | 2/2001 | Ishihara et al. |
| 6,242,915 B1 | 6/2001 | Hurd |
| 6,263,230 B1 | 7/2001 | Haynor et al. |
| 6,267,734 B1 | 7/2001 | Ishibashi et al. |
| 6,289,233 B1 | 9/2001 | Dumoulin et al. |
| 6,309,355 B1 | 10/2001 | Cain et al. |
| 6,334,846 B1 | 1/2002 | Ishibashi et al. |
| 6,374,132 B1 | 4/2002 | Acker et al. |
| 6,377,834 B1 | 4/2002 | Zhou et al. |
| 6,392,330 B1 | 5/2002 | Zloter et al. |
| 6,397,094 B1 | 5/2002 | Ludeke et al. |
| 6,413,216 B1 | 7/2002 | Cain et al. |
| 6,419,648 B1 | 7/2002 | Vitek et al. |
| 6,424,597 B1 | 7/2002 | Bolomey et al. |
| 6,425,867 B1 | 7/2002 | Vaezy et al. |
| 6,428,532 B1 | 8/2002 | Doukas et al. |
| 6,461,314 B1 | 10/2002 | Pant et al. |
| 6,475,150 B2 | 11/2002 | Haddad |
| 6,478,739 B1 | 11/2002 | Hong |
| 6,506,154 B1 | 1/2003 | Ezion et al. |
| 6,506,171 B1 | 1/2003 | Vitek et al. |
| 6,511,428 B1 | 1/2003 | Azuma et al. |
| 6,522,142 B1 | 2/2003 | Freundlich et al. |
| 6,523,272 B1 | 2/2003 | Morales |
| 6,542,767 B1 | 4/2003 | McNichols et al. |
| 6,559,644 B2 | 5/2003 | Froundlich et al. |
| 6,566,878 B1 | 5/2003 | Komura et al. |
| 6,582,381 B1 | 6/2003 | Yehezkeli et al. |
| 6,599,256 B1 | 7/2003 | Acker et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,618,608 B1 | 9/2003 | Watkins et al. |
| 6,618,620 B1 | 9/2003 | Freundlich et al. |
| 6,626,854 B2 | 9/2003 | Friedman et al. |
| 6,626,855 B1 | 9/2003 | Weng et al. |
| 6,629,929 B1 | 10/2003 | Jago et al. |
| 6,645,162 B2 | 11/2003 | Friedman et al. |
| 6,666,833 B1 | 12/2003 | Friedman et al. |
| 6,676,601 B1 | 1/2004 | Lacoste et al. |
| 6,679,855 B2 | 1/2004 | Horn et al. |
| 6,705,994 B2 | 3/2004 | Vortman et al. |
| 6,719,694 B2 | 4/2004 | Weng et al. |
| 6,733,450 B1 | 5/2004 | Alexandrov et al. |
| 6,735,461 B2 | 5/2004 | Vitek et al. |
| 6,761,691 B2 | 7/2004 | Tsuzuki |
| 6,770,031 B2 | 8/2004 | Hynynen et al. |
| 6,770,039 B2 | 8/2004 | Zhong et al. |
| 6,788,619 B2 | 9/2004 | Calvert |
| 6,790,180 B2 | 9/2004 | Vitek |
| 6,824,516 B2 | 11/2004 | Batten et al. |
| 6,825,667 B1 | 11/2004 | Tsuda |
| 6,951,540 B2 | 10/2005 | Ebbini et al. |
| 6,961,606 B2 | 11/2005 | DeSilets et al. |
| 7,001,379 B2 | 2/2006 | Behl et al. |
| 7,062,415 B2 | 6/2006 | Whitefield et al. |
| 7,077,820 B1 | 7/2006 | Kadziauskas et al. |
| 7,094,205 B2 | 8/2006 | Marmarelis |
| 7,128,711 B2 | 10/2006 | Medan et al. |
| 7,175,596 B2 | 2/2007 | Vitek et al. |
| 7,175,599 B2 | 2/2007 | Hynynen et al. |
| 7,264,592 B2 | 9/2007 | Shehada |
| 7,264,597 B2 | 9/2007 | Cathignol |
| 7,267,650 B2 | 9/2007 | Chow et al. |
| 7,344,509 B2 | 3/2008 | Hynynen et al. |
| 7,359,745 B2 | 4/2008 | Lewin et al. |
| 7,377,900 B2 | 5/2008 | Vitek et al. |
| 7,412,835 B2 | 8/2008 | Legall et al. |
| 7,505,808 B2 | 3/2009 | Anderson et al. |
| 7,510,536 B2 | 3/2009 | Foley et al. |
| 7,511,501 B2 | 3/2009 | Wexler |
| 7,535,794 B2 | 5/2009 | Prus et al. |
| 7,553,284 B2 | 6/2009 | Vaitekunas |

(56) References Cited

U.S. PATENT DOCUMENTS

| | | | |
|---|---|---|---|
| 7,603,162 | B2 | 10/2009 | Danz et al. |
| 7,611,462 | B2 | 11/2009 | Vortman et al. |
| 7,652,410 | B2 | 1/2010 | Prus |
| 7,699,780 | B2 | 4/2010 | Vitek et al. |
| 8,024,025 | B2 | 9/2011 | Mallozzi et al. |
| 8,368,401 | B2 | 2/2013 | Levy et al. |
| 8,482,285 | B2 | 7/2013 | Grissom et al. |
| 2001/0031922 | A1 | 10/2001 | Weng et al. |
| 2002/0035779 | A1 | 3/2002 | Krieg et al. |
| 2002/0082589 | A1 | 6/2002 | Friedman et al. |
| 2003/0004439 | A1 | 1/2003 | Pant et al. |
| 2003/0060820 | A1 | 3/2003 | Maguire et al. |
| 2003/0187371 | A1 | 10/2003 | Vortman et al. |
| 2004/0030251 | A1 | 2/2004 | Ebbini et al. |
| 2004/0068186 | A1 | 4/2004 | Ishida et al. |
| 2004/0122323 | A1 | 6/2004 | Vortman et al. |
| 2004/0210134 | A1 | 10/2004 | Hynynen et al. |
| 2005/0033201 | A1 | 2/2005 | Takahashi et al. |
| 2005/0096542 | A1 | 5/2005 | Weng et al. |
| 2005/0203444 | A1 | 9/2005 | Schonenberger et al. |
| 2005/0251046 | A1 | 11/2005 | Yamamoto et al. |
| 2006/0052661 | A1 | 3/2006 | Gannot et al. |
| 2006/0052701 | A1 | 3/2006 | Carter et al. |
| 2006/0058678 | A1 | 3/2006 | Vitek et al. |
| 2006/0106300 | A1 | 5/2006 | Seppenwoolde et al. |
| 2006/0184163 | A1 | 8/2006 | Breen et al. |
| 2007/0055140 | A1 | 3/2007 | Kuroda |
| 2007/0239062 | A1 | 10/2007 | Chopra et al. |
| 2009/0096450 | A1 | 4/2009 | Roland |
| 2009/0275821 | A1* | 11/2009 | Mallozzi et al. ............... 600/412 |
| 2011/0046472 | A1 | 2/2011 | Schmidt et al. |
| 2011/0046475 | A1 | 2/2011 | Assif et al. |
| 2011/0175615 | A1 | 7/2011 | Grissom et al. |
| 2012/0071746 | A1 | 3/2012 | Vortman et al. |
| 2013/0119984 | A1 | 5/2013 | Levy et al. |

FOREIGN PATENT DOCUMENTS

| | | |
|---|---|---|
| EP | 1582886 | 10/2005 |
| EP | 1774920 A1 | 4/2007 |
| FR | 2806611 A1 | 9/2001 |
| JP | 11313833 A | 11/1999 |
| WO | WO-9100059 A1 | 1/1991 |
| WO | WO-9852465 A1 | 11/1998 |
| WO | 99/21024 A1 | 4/1999 |
| WO | WO-0031614 A1 | 6/2000 |
| WO | WO-0166189 A1 | 9/2001 |
| WO | WO-0180709 A2 | 11/2001 |
| WO | WO-0258791 A1 | 8/2002 |
| WO | WO-03/013654 A1 | 2/2003 |
| WO | WO-03097162 A2 | 11/2003 |
| WO | WO-03098232 A2 | 11/2003 |
| WO | WO-2005058029 A2 | 6/2005 |
| WO | WO-2006018837 A2 | 2/2006 |
| WO | WO-2006025001 A1 | 3/2006 |
| WO | WO-2006087649 A1 | 8/2006 |
| WO | WO-2007073551 A1 | 6/2007 |
| WO | WO-2008050278 A1 | 5/2008 |
| WO | WO-2008075203 A2 | 6/2008 |
| WO | WO-2008/119054 | 10/2008 |
| WO | WO-2009/055587 | 4/2009 |

OTHER PUBLICATIONS

Botros et al., "A hybrid computational model for ultrasound phased-array heating in presence of strongly scattering obstacles," IEEE Trans. on Biomed. Eng., vol. 44, No. 11, pp. 1039-1050 (Nov. 1997).
Cain et al., "Concentric-ring and Sector-vortex Phased-array Applicators for Ultrasound Hperthermia," IEEE Trans. on Microwave Theory & Techniques, vol. MTT-34, No. 5, pp. 542-551 (May 1986).
Cline et al., "Focused US system for MR imaging-guide tumor ablation," Radiology, v. 194, No. 3, pp. 731-738 (Mar. 1995).
Cline et al., "MR Temperature mapping of focused ultrasound surgery," Magnetic Resonance in Medicine, vol. 32, No. 6, pp. 628-636 (1994).
Cline et al., "Simultaneous magnetic resonance phase and magnitude temperature maps in muscle," Magnetic Resonance in Medicine, vol. 35, No. 3, pp. 309-315 (Mar. 1996).
Daum et al., "Design and evaluation of a feedback based phased array system for ultrasound surgery," IEEE Trans. Ultrason. Ferroelec. Freq. Control, vol. 45, No. 2, pp. 431-434 (1998).
Fjield et al, "The Combined Concentric-ring and Sector-vortex Phased Array for MRI Guided Ultrasound Surgery," IEEE Trans. on Ultrasonics, Ferroelectrics and Freq. Cont., vol. 44, No. 5, pp. 1157-1167 (Sep. 1997).
Huber et al., "A New Noninvasive Approach in Breast Cancer Therapy Using Magnetic Resonance Imaging-Guided Focussed Ultrasound Surgery," Cancer Research 61, 8441-8447 (Dec. 2001).
International Preliminary Report on Patentability in International Patent Application No. PCT/IB2004/001512, mailed Dec. 8, 2005.
International Search Report and Written Opinion in International Patent Application No. PCT/IB2004/001498, dated Aug. 31, 2004.
International Search Report and Written Opinion in International Patent Application No. PCT/IB2005/002273, mailed Dec. 20, 2005.
International Search Report and Written Opinion in International Patent Application No. PCT/IB2005/002413, mailed Nov. 22, 2005.
International Search Report and Written Opinion in International Patent Application No. PCT/IB2006/001641, mailed Sep. 25, 2006.
International Search Report and Written Opinion in International Patent Application No. PCT/IB2006/003300, mailed Feb. 14, 2008.
International Search Report and Written Opinion in International Patent Application No. PCT/IB2007/001079, mailed Dec. 10, 2007.
International Search Report and Written Opinion in International Patent Application No. PCT/IB2007/002134, mailed Dec. 13, 2007.
International Search Report and Written Opinion in International Patent Application No. PCT/IB2007/002140, mailed Dec. 29, 2008.
International Search Report and Written Opinion in International Patent Application No. PCT/IB2008/003069, mailed Apr. 27, 2009.
Jolesz et al., "Integration of interventional MRI with computer-assisted surgery," J. Magnetic Resonance Imaging. 12:69-77 (2001).
Maxwell et al', "Noninvasive thrombolysis using pulsed ultrasound cavitation therapy—Histotripsy," Abstract, U.S. Natl. Lib. of Med., NIH, Ultrasound Med. Biol. (Oct. 23, 2009).
McDannold et al., "MRI evaluation of thermal ablation of tumors and focused ultrasounds," JMRI vol. 8, No. 1, pp. 91-100 (1998).
McDannold et al., "Magnetic resonance acoustic radiation force imaging," Med. Phys. vol. 35, No. 8, pp. 3748-3758 (Aug. 2008).
Partial International Search Report and Written Opinion in International Patent Application No. PCT/IB2007/001079, dated Sep. 25, 2007.
Vykhodtseva et al., "MRI detection of the thermal effects of focused ultrasound on the brain," Ultrasound in Med. & Biol., vol. 26, No. 5, pp. 871-880 (2000).
Written Opinion in International Patent Application No. PCT/IL01/00340, mailed Feb. 24, 2003.
Written Opinion in International Patent Application No. PCT/IL02/00477, mailed Feb. 25, 2003.
Written Opinion in International Patent Application No. PCT/IB03/05551, mailed Sep. 10, 2004.
"How is Ablatherm treatment performed?" http://www.edap-hifu.com/eng/physicians/hifu/3c_treatment_treat-description.htm, accessed Jan. 3, 2003.
"What is HIFU? HIFU: High Intensity Focused Ultrasound," http://www.edap-hifu.com/eng/physicians/hifu2a _hifu_overview.htm, accessed Jan. 3, 2003.
"What are the physical principles?" http://www.edap-hifu.com/eng/physicians/hifu/2c_hifu_physical.htm, accessed Jan. 3, 2003.
"How does HIFU create a lesion?" http://www.edap-hifu.com/eng/physicians/hifu/2d_hifu_lesion.htm, accessed Jan. 3, 2003.
"Prostate Cancer Phase I Clinical Trials Using High Intensity Focused Ultrasound (HIFU)," Focus Surgery, http://www.focus-surgery.com/PCT%20Treatment%20with%20HIFU.htm, accessed Jan. 3, 2003.
"Abstract" Focus Surgery, http://www.focus-surgery.com/Sanghvi.htm, accessed Jan. 3, 2003.
Exablate 2000 Specification, InSightec, Ltd. (2 pages).
FDA Approves Exablate 2000 as Non-invasive surgery for Fibroids, Oct. 22, 2004.

(56) References Cited

OTHER PUBLICATIONS

International Search Report and Written Opinion in International Patent Application No. PCT/IB2010/000189, mailed Jun. 1, 2010.
International Search Report for PCT/IB03/05551 completion date Mar. 2, 2004 (5 pages).
International Search Report and Written Opinion in Internation Patent Application No. PCT/IB2010/000971, mailed Jul. 29, 2010 (9 pages).
Charles Mougenot, et al, "MR Monitoring of the Near-Field HIFU Heating," 8th International Symposium on Therapeutic Ultrasound, edited by E. S. Ebbini, University of Minnesota, Sep. 10-13, 2009.
Max O. Kohler, et al, "Volumetric HFU Ablation guided by Multiplane MRI Thermometry," 8th International Symposium on Therapeutic Ultrasound, edited by E. S. Ebbini, University of Minnesota, Sep. 10-13, 2009.
Kowalski et al, "Optimization of electromagnetic phased-arrays for hyperthermia via magnetic resonance temperature estimation," Biomedical Engineering, IEEE Transactions on vol. 49, Issue 11, Nov. 2002, pp. 1229-1241.
Partial Search Report mailed Feb. 21, 2011 for International Application No. PCT/IB32010/002606 (3 pages).
Bouchard et al., "Magnetic Resonance Imaging of Thermal Coagulation Effects in a Phantom for Calibrating Thermal Therapy Devices," Medical Physics, vol. 27, No. 5, pp. 1141-1145 (May 1, 2000).
Wlodarczyk et al, "Corrections and Calibration of MR Thermography for Hyperthermia Monitoring in the Hyperthermia/MR Hybrid System," Proceedings of the Intl. Soc. for Magnetic Resonance in Medicine, 12th Scientific Meeting and Exhibition, p. 977 (May 1, 2004).
Wang et al., "Sensitivity Study of MR-Based Temperature Mapping at 7T," Proceedings of the Intl. Society for Magnetic Resonance in Medicine, Joint Annual Meeting ISMRM-ISMRM, p. 3377 (May 5, 2007).
McDannold et al., "Usefulness of MR Imaging-Derived Thermometry and Dosimetry in Determining the Threshold for Tissue Damage Induced by Thermal Surgery in Rabbits," Radiology, vol. 216 pp. 517-523 (2000).
Suprijanto et al., "Displacement Correction Scheme for MR-Guided Interstitial Laser Therapy," Ellis RE, Peters TM (Eds.): "MiCCAI 2003, LNCS 2879," pp. 399-407 (2003).
Shmatukha et al., "Correction of Proton Resonance Frequency Shift Proton Resonance Frequency Shift Temperature Maps for Magnetic Field Disturbances Caused by Breathing; Correction of Proton Resonance Frequency Shift Temperature Maps," Physics in Medicine and Biology, vol. 51, No. 18 pp. 4689-4705 (Sep. 21, 2006).
De Senneville et al., "An Optimised Multi-Baseline Approach for On-Line MR-Temperature Monitoring on Commodity Graphics Hardware," Biomedical Imaging, pp. 1513-1516 (May 14, 2008).
Beerlage et al., "Current Status of Minimally Invasive Treatment Options for Localized Prostate Carcinoma," European Urology, vol. 47, No. 1 pp. 2-13 (Jan. 2000).
Boyd et al., "Convex Optimization," Cambridge University Press, UK (2004).
Chartrand et al., "Iteratively Reweighted Algorithms for Compressive Sensing," IEEE ICASSP, pp. 3869-3872 (Apr. 2008).
Funai et al., "Regularized Field Map Estimation in MRI," IEEE Trans.Med. Imaging, vol. 27, No. 10, pp. 1484-1494 (Oct. 2008).
Grissom et al., "Hybrid Referenceless and Multibaseline Subtraction MR Thermometry for Monitoring Thermal Therapies in Moving Organs," Medical Physics, vol. 37, No. 9. pp. 5014-5026 (Sep. 2010).
Grissom et al. "Reference-less MR Thermometry Using Iteratively-Reweighted $\ell$ 1 Regression," Proc. Intl. Soc. Mag. Reson. Med., vol. 17, p. 444 (2009).
Grissom et al., "Regularized Multicoil MR Thermometry," Proc. Intl. Soc. Mag. Reson. Med., vol. 17, p. 2516 (2009).
Grissom et al., "Regularized Referenceless Temperature Estimation in PRF-Shift MR Thermometry," IEEE, pp. 1235-1238 (2009).
Holbrook et al., "Real-Time MR Thermometry for Monitoring HIFU Ablations of the Liver," Magnetic Resonance in Medicine, vol. 63, pp. 365-373 (2010).
Ishihara et al., "A Precise and Fast Temperature Mapping Using Water Proton Chemicl Shift," MRM, vol. 34, pp. 814-823 (1995).
Kokuryo et al., "Method for Target Tracking in Focused Ultrasound Surgery of Liver Using Magnetic Resonance Filtered Venography," IEEE EMBS, pp. 2614-2617 (2007).
Kuroda et al., "Optimization of Self-Reference Thermometry Using Complex Field Estimation," Magnetic Resonance in Medicine, vol. 56, pp. 835-843 (2006).
Larson et al., "Histological Changes of Minimally Invasive Procedures for the Treatment of Benign Prostatic Hyperplasia and Prostate Cancer: Clinical Implications," The Journal of Urology, vol. 170, pp. 12-19 (Jul. 2003).
Mougenot et al., "MR monitoring of the near-field HIFU heating," 8th Intl. Symp. on Therapeutic Ultrasound, edited by E.S. Ebbini, U. of Minn. (Sep. 2009).
Nayak et al., "Real-Time Cardiac MRI at 3 Tesla," Magnetic Resonance in Medicine, vol. 51, pp. 655-660 (2004).
Rieke et al., "Referenceless PRF Shift Thermometry," Magnetic Resonance in Medicine, vol. 51, pp. 1223-1231 (2004).
Roujol et al., "Advanced in Real-Time MR Temperature Mapping of the Human Heart," Proc. Intl. Soc. Mag. Reson. Med. vol. 17, p. 443 (2009).
Shinohara "Thermal Ablation of Prostate Diseases: Advantages and Limitations," Int. Journal of Hyperthermia, vol. 20, No. 7, pp. 679-697 (Nov. 2004).
Soher et al., "Correcting for BO Field Drift in MR Temperature Mapping with Oil References," Proceedings of the Intl. Society for Magnetic Resonance in Medicine (May 2008).
Vigen et al., "Triggered, Navigated, Multi-Baseline Method for Proton Resonance Frequency Temperature Mapping with Respiratory Motion," Magnetic Resonance in Medicine, vol. 50, pp. 1003-1010 (2003).
Examination Report in European Patent Application No. 11778686.3, mailed on Mar. 3, 2014, 8 pages.
International Application Serial No. PCT/IB2010/003038, International Search Report and Written Opinion mailed on Mar. 31, 2011, 20 pages.
International Application Serial No. PCT/IB2011/002450, International Search Report and Written Opinion mailed on Feb. 2, 2011, 20 pages.
International Application Serial No. PCT/US2010/046429, International Search Report and Written Opinion mailed on Dec. 7, 2010, 12 pages.
International Application Serial No. PCT/US2011/021657, International Search Report and Written Opinion mailed on Aug. 16, 2011, 21 pages.
Candes et al., "Enhancing Sparsity by Reweighted $\ell$ 1 Minimization", Journal of Fourier Analysis and Applications, vol. 14, No. 5, 2007, pp. 877-905.
Depoorter et al., "The Proton-Resonance-Frequency-Shift Method Compared with Molecular Diffusion for Quantitative Measurement of Two-Dimensional Time-Dependent Temperature Distribution in a Phantom", Journal of Magnetic Resonance, Series B, vol. 103, No. 3, Mar. 1994, pp. 234-241.
Fuentes et al. "Real-Time Bioheat Transfer Models for Computer Driven MR guided LITT", Proceedings of the International Society for Magnetic Resonance in Medicine, 18th Scientific Meeting and Exhibition, Stockholm, Sweden, May 1-7, 2010, vol. 18, p. 4141.
Incropera et al., "The Bioheat Equation", Fundamentals of Heat and Mass Transfer, 6th Edition, Chapter 3, Section 3.7 and Appendix A, table A.3, 2007, 14 pages.
Pennes, Harry H., "Analysis of Tissue and Arterial Blood Temperatures in the Resting Human Forearm", Journal of Applied Physiology, vol. 1, No. 2, Aug. 1948, pp. 93-122.
Peters et al., "Proton-Resonance Frequency Shift MR Thermometry is Affected by Changes in the Electrical Conductivity of Tissue", Magnetic Resonance in Medicine, vol. 43, No. 1, Jan. 2000, pp. 62-71.

(56) References Cited

OTHER PUBLICATIONS

Shmatukha et al., "Correction of Proton Resonance frequency Shift Temperature Maps for Magnetic Field Disturbances Using Fat Signal", Journal of Magnetic Resonance Imaging, vol. 25, No. 3, Mar. 2007, pp. 579-587.

De Senneville et al., "Real-Time Adaptive methods for Treatment of Mobile Organs by MRI-Controlled High-Intensity Focused Ultrasound," Magnetic Resonance in Medicine, vol. 57, pp. 319-330 (2007).

DeZwart et al., "On-Line Correction and Visualization of Motion During MRI-Controlled Hyperthermia," Magnetic Resonance in Medicine, vol. 45, No. 1, pp. 128-137 (Jan. 1, 2001).

International Search Report and Written Opinion mailed May 20, 2011 for International Application No. PCT/IB2010/002606 (24 pages).

Suprijanto et al., "Inter-frame Motion Correction for MR Thermometry," Medical Image Computing and Computer-Assisted Intervention—MICCAI 2005 Lecture Notes in Computer Science, pp. 580-588 (Jan. 2005).

De Senneville et al., "Motion Correction in MR Thermometry of Abdominal Organs: A Comparison of the Referenceless vs. the Multibaseline Approach," Magnetic Resonance in Medicine, vol. 64, pp. 1373-1381 (Jul. 2010).

Li et al., "An Internal Reference Model-Based PRF Temperature Mapping Method with Cramer-Rao Lower Bound Noise Performance Analysis," Magnetic Resonance in Medicine, vol. 62, pp. 1251-1260 (Sep. 2009).

Wissler, "Pennes' 1948 Paper Revisited," Journal of Applied Physiology, vol. 85, pp. 35-41 (1998).

Romero-Méndez et al., "Analytical Solution of the Pennes Equation for Burn-Depth Determination From Infrared Thermographs," Mathematical Medicine and Biology, vol. 27, pp. 21-38 (Jul. 2009).

Dragonu et al., "Perfusion Calculation Based on MR-Temperature Maps and Focused Ultrasound Heating. Theoretical and Experimental Study," Intl. Society for Magnetic Resonance in Medicine, vol. 16, p. 1223 (May 3, 2008).

Chopra et al., "Method for MRI-Guided Conformal Thermal Therapy of Prostate with Planar Transurethral Ultrasound Heating Applicators; Method for Conformal Prostate Thermal Therapy," Physics in Medicine and Biology, vol. 50, No. 21, pp. 4957-4975 (Nov. 7, 2005).

Salomir et al., "Hyperthermia by MR-Guided Focused Ultrasound: Accurate Temperature Control Based on Fast MRI and a Physical Model of Local Energy Deposition and Heat Conduction," Magnetic Resonance in Medicine, vol. 43, No. 3, pp. 342-347 (Mar. 1, 2000).

Rieke et al., "Referenceless MR Thermometry for Monitoring Thermal Ablation in the Prostate," IEEE Transactions on Medical Imaging, pp. 813-821 (Jun. 1, 2007).

\* cited by examiner

TECHNIQUES FOR TEMPERATURE MEASUREMENT AND CORRECTIONS IN LONG-TERM MAGNETIC RESONANCE THERMOMETRY

FIELD OF THE INVENTION

The present invention relates generally to magnetic resonance (MR) imaging, and more particularly, to techniques for temperature measurement and corrections in long-term MR thermometry.

BACKGROUND OF THE INVENTION

MR imaging of internal body tissues may be used for numerous medical procedures, including diagnosis and surgery. In general terms, MR imaging starts by placing a subject in a relatively uniform, static magnetic field. The static magnetic field causes hydrogen nuclei spins to align and precess about the general direction of the magnetic field. Radio frequency (RF) magnetic field pulses are then superimposed on the static magnetic field to cause some of the aligned spins to alternate between a temporary high-energy non-aligned state and the aligned state, thereby inducing an RF response signal, called the MR echo or MR response signal. It is known that different tissues in the subject produce different MR response signals, and this property can be used to create contrast in an MR image. An RF receiver detects the duration, strength, and source location of the MR response signals, and such data are then processed to generate tomographic or three-dimensional images.

MR imaging can also be used effectively during a medical procedure to assist in locating and guiding medical instruments. For example, a medical procedure can be performed on a patient using medical instruments while the patient is in an MRI machine. The medical instruments may be for insertion into a patient or they may be used externally but still have a therapeutic or diagnostic effect. For instance, the medical instrument can be an ultrasonic device, which is disposed outside a patient's body and focuses ultrasonic energy to ablate or necrose tissue or other material on or within the patient's body. The MRI machine preferably produces images at a high rate so that the location of the instrument (or the focus of its effects) relative to the patient may be monitored in real-time (or substantially in real-time). The MRI machine can be used for both imaging the targeted body tissue and locating the instrument, such that the tissue image and the overlaid instrument image can help track an absolute location of the instrument as well as its location relative to the patient's body tissue.

MR imaging can further provide a non-invasive means of quantitatively monitoring in vivo temperatures. This is particularly useful in the above-mentioned MR-guided focused ultrasound (MRgFUS) treatment or other MR-guided thermal therapy where temperature of a treatment area should be continuously monitored in order to assess the progress of treatment and correct for local differences in heat conduction and energy absorption. The monitoring (e.g., measurement and/or mapping) of temperature with MR imaging is generally referred to as MR thermometry or MR thermal imaging.

Among the various methods available for MR thermometry, the proton-resonance frequency (PRF) shift method is often preferred due to its excellent linearity with respect to temperature change, near-independence from tissue type, and good sensitivity. The PRF shift method is based on the phenomenon that the MR resonance frequency of protons in water molecules changes linearly with temperature. Since the frequency change is small, only −0.01 ppm/° C. for bulk water and approximately −0.0096 to −0.013 ppm/° C. in tissue, the PRF shift is typically detected with a phase-sensitive imaging method in which the imaging is performed twice: first to acquire a baseline phase image prior to a temperature change and then to acquire a second phase image after the temperature change, thereby capturing a small phase change that is proportional to the change in temperature.

A phase image, for example, may be computed from MR image data, and a temperature-difference map relative to the baseline image may be obtained by (i) subtracting, on a pixel-by-pixel basis, the phase image corresponding to the baseline from the phase image corresponding to a subsequently obtained MR image, and (ii) converting phase differences into temperature differences based on the PRF temperature dependence.

Unfortunately, changes in phase images do not arise uniquely from temperature changes. Various non-temperature-related factors, such as changes in a local magnetic field due to nearby moving metal, magnetic susceptibility changes in a patient's body due to breathing or movement, and magnet or shim drifts can all lead to confounding phase shifts that may render a phase-sensitive temperature measurement invalid. The changes in magnetic field associated with magnet drift and patient motion are often severe enough to render temperature measurements made using the above-mentioned phase-sensitive approach useless.

Spurious phase shifts can be quite significant when temperature changes are monitored over a long time period, such as during a lengthy treatment procedure. As the elapsed time between the initial baseline phase image and the actual temperature measurement increases, concurrent (and non-temperature-related) changes in magnetic field are more likely to occur, impairing the accuracy of temperature measurement. For example, in existing MR-guided thermal treatment procedures, it is often assumed that the main magnetic field and gradient field are sufficiently stable during the treatment and that the pre-treatment temperature of a target area is known, such that any phase shift is assumed to be due exclusively to change in temperature. These assumptions might be valid in certain MRgFUS procedures where tissues of interest lie deep within a patient's body or where heating periods are short (e.g., less than a minute per heating period, followed by a cooling-down period allowing the tissues to return to body temperature). However, the above-mentioned assumptions do not hold up when heating periods are relatively long or with slower heating methods (e.g., radiofrequency and laser heating). Nor are these assumptions valid when an initial tissue temperature is unknown, such as when the treatment area is close to skin surface or is actively cooled.

Also, in some applications of MR thermometry, it may be critical or desirable to measure absolute temperature(s) instead of a simple change in temperature. For example, in a prostate treatment with MRgFUS, an absolute temperature of the treatment area may be required in order to accurately calculate a thermal dose. However, if the patient's rectum is actively cooled for safety reasons, there will be a gradual temperature change between the cooled rectal wall and the inner tissue of the prostate. In general, this temperature profile cannot be estimated with sufficient accuracy due to variability of tissue properties among patients (e.g., differences in perfusion), so an absolute temperature measurement becomes necessary. Another example relates to an MRgFUS treatment of soft tissue tumors, where a significant amount of time may be spent waiting for a heated tissue to cool down after each delivery of ultrasonic energy. Although long cooling periods may not be necessary for safety or efficacy reasons, they are still deemed necessary because the temperature measurement during the next energy delivery (sonication) relies on the assumption that the heated tissue has returned to body temperature. If an absolute temperature of the heated tissue were measured, subsequent sonications could start sooner and thus the overall treatment time could be significantly shortened.

In view of the foregoing, it may be understood that there are significant problems and shortcomings associated with current PRF techniques.

SUMMARY

Embodiments of the present invention provide for measurement of absolute temperatures as well as phase shift corrections in relatively long-term MR thermometry. In particular, a known temperature distribution is established in an MR imaging area as a baseline for absolute temperature measurement. Phase shifts that arise from magnetic field and magnetic field gradient drifts are detected in one or more portions of the MR imaging area with known or constant temperature(s) and then extrapolated to other portions of the MR imaging area, facilitating correction of temperature measurements in an area of interest. Temperature measurement problems due to movement or deformation of the area of interest are solved by registering an initial baseline temperature map and acquiring a new phase reference.

Due to the linear relationship between a PRF shift and the corresponding temperature change, it is mathematically equivalent to process or manipulate phase differences or the corresponding temperature map (which reflects changes in temperature proportional to the phase differences). Therefore, it should be appreciated by those skilled in the art that the MR thermal-imaging-related computations described herein may be performed in either the phase domain or in temperature domain, or both, depending on implementational convenience. Thus, when reference is herein made to determining corrections based on (or otherwise manipulating) phase images, it is to be understood that the requisite computational operations can be applied to the phase difference image or to the corresponding temperature map. Similarly, corrections may be applied to phase difference image or to a temperature map, or both.

In one particular exemplary embodiment, a method of performing PRF-based MR temperature measurement may comprise the steps of acquiring a first phase image of an MR imaging area having a known temperature distribution, where the MR imaging area comprises an area of interest, and acquiring a second phase image of the MR imaging area subsequent to the acquisition of the first phase image. The method may also comprise the step of determining, from differences between the second phase image and the first phase image (or from a resulting temperature map), first correction(s) in one or more portions of the MR imaging area that have experienced a known or clinically insignificant change in temperature since the acquisition of the first phase image. The method may further comprise the step of determining second correction(s) in at least the area of interest by extrapolating the first correction(s). Additionally, the method may comprise the step of assigning a first set of one or more absolute temperatures to the area of interest based at least in part on (i) the known temperature distribution and (ii) the second correction(s).

In another particular exemplary embodiment, a system for performing PRF-based MR temperature measurement may comprise an MRI unit. The system may also comprise a control module in communication with the MRI unit, and configured to cause the MRI unit to acquire a first phase image of an MR imaging area having a known temperature distribution and comprising an area of interest. The control module may further cause the MRI unit to acquire a second phase image of the MR imaging area subsequent to the acquisition of the first phase image. The system may further comprise a processor module having access to image data acquired by the MRI unit, and configured to determine, from the second phase image, first correction(s) in one or more portions of the MR imaging area that have experienced a known or clinically insignificant change in temperature since the acquisition of the first phase image, determine second correction(s) in at least the area of interest by extrapolating the first correction(s), and assign a first set of one or more absolute temperatures to the area of interest based at least in part on (i) the known temperature distribution and (ii) the second correction(s).

In yet another particular exemplary embodiment, a computer-readable medium storing computer-executable codes for causing at least one processor to correct PRF-based MR temperature measurement may comprise computer-executable code adapted to acquire a first phase image of an MR imaging area having a known temperature distribution and an area of interest, and computer-executable code adapted to acquire a second phase image of the MR imaging area subsequent to the acquisition of the first phase image. The computer-readable medium may also comprise computer-executable code adapted to determine, from the second phase image, first correction(s) in one or more portions of the MR imaging area that have experienced a known or clinically insignificant change in temperature since the acquisition of the first phase image. The computer-readable medium may further comprise computer-executable code adapted to determine second correction(s) in at least the area of interest by extrapolating the first correction(s). The computer-readable medium may additionally comprise computer-executable code adapted to assign a first set of one or more absolute temperatures to the area of interest based at least in part on (i) the known temperature distribution and (ii) the second correction(s).

In still another particular exemplary embodiment, a method of performing PRF-based MR temperature measurement may comprise the steps of obtaining a temperature distribution in an area of interest; detecting a movement and/or deformation of the area of interest; transforming the temperature distribution into a new temperature distribution through image registration based on the detected movement and/or deformation; acquiring a first phase image of the area of interest subsequent to the detected movement and/or deformation; acquiring a second phase image of the area of interest subsequent to the acquisition of the first phase image; and assigning one or more absolute temperatures of the area of interest based at least in part on (i) the new temperature distribution and (ii) a difference between the second phase image and the first phase image.

The present invention will now be described in more detail with reference to exemplary embodiments thereof as shown in the accompanying drawings. While the present invention is described below with reference to exemplary embodiments, it should be understood that the present invention is not limited thereto. Those of ordinary skill in the art having access to the teachings herein will recognize additional implementations, modifications, and embodiments, as well as other fields of use, which are within the scope of the present invention as described herein, and with respect to which the present invention may be of significant utility.

BRIEF DESCRIPTION OF THE DRAWINGS

In order to facilitate a fuller understanding of the present invention, reference is now made to the accompanying drawings, in which like elements are referenced with like numerals. These drawings should not be construed as limiting the present invention, but are intended to be exemplary only.

DETAILED DESCRIPTION

Embodiments of the present invention improve the utility and robustness of MR thermometry, as described below, to measure absolute temperatures and compensate for phase shifts that arise from factors other than temperature changes.

Figure 1:
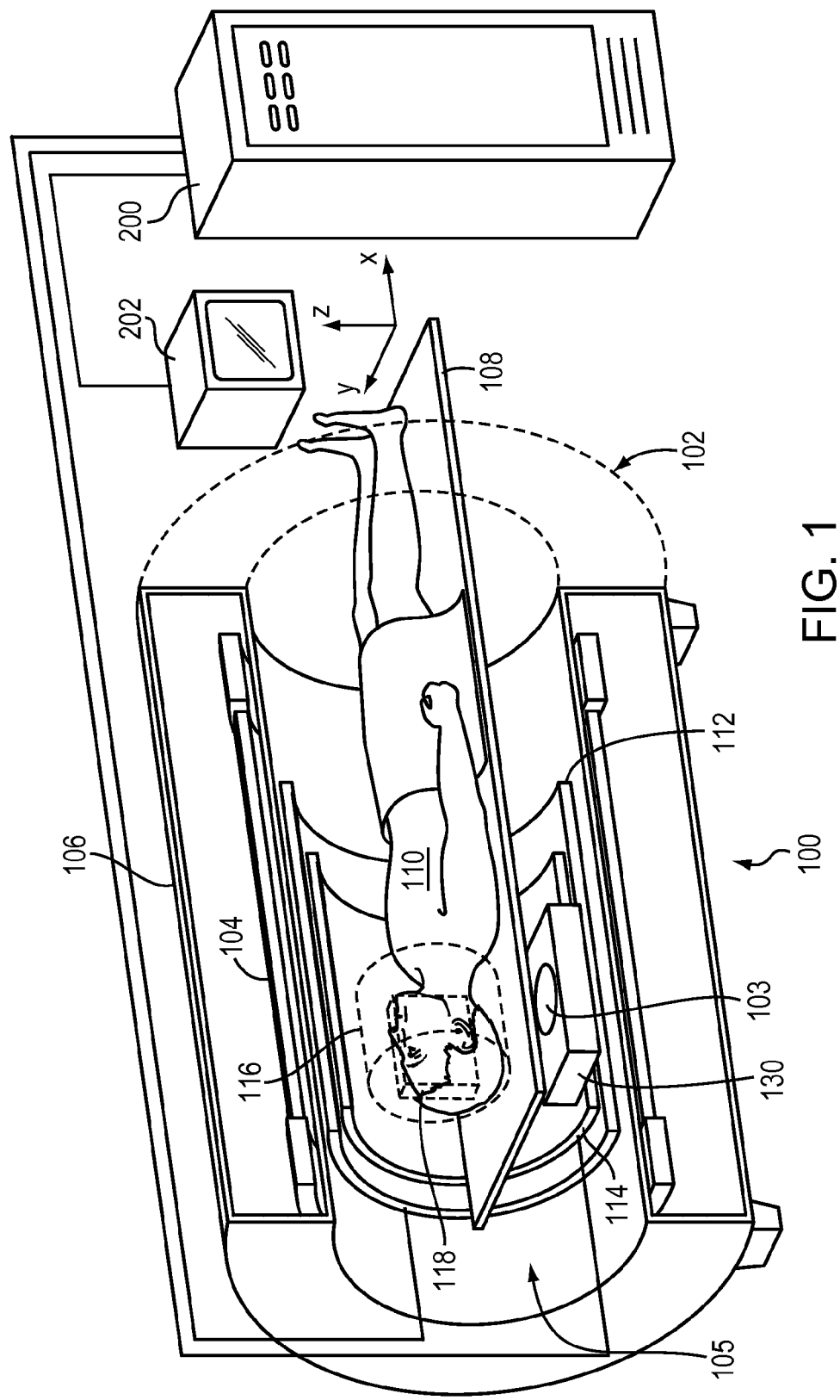
FIG. 1 shows an exemplary MRI system in or for which the techniques for temperature measurement and corrections in accordance with the present invention may be implemented.

FIG. 1 shows an exemplary MRI system in or for which the techniques for temperature measurement and corrections in accordance with the present invention may be implemented. The illustrated MRI system 100 comprises an MRI machine 102. If an MR-guided procedure is being performed, a medical device 103 may be disposed within the bore of the MRI machine 102. Since the components and operation of the MRI machine are well-known in the art, only some basic components helpful in the understanding of the system 100 and its operation will be described herein.

The MRI machine 102 typically comprises a cylindrical electromagnet 104, which generates a static magnetic field within a bore 105 of the electromagnet 104. The electromagnet 104 generates a substantially homogeneous magnetic field within an imaging region 116 inside the magnet bore 105. The electromagnet 104 may be enclosed in a magnet housing 106. A support table 108, upon which a patient 110 lies, is disposed within the magnet bore 105. A region of interest 118 within the patient 110 may be identified and positioned within the imaging region 116 of the MRI machine 102.

A set of cylindrical magnetic field gradient coils 112 may also be provided within the magnet bore 105. The gradient coils 112 also surround the patient 110. The gradient coils 112 can generate magnetic field gradients of predetermined magnitudes, at predetermined times, and in three mutually orthogonal directions within the magnet bore 105. With the field gradients, different spatial locations can be associated with different precession frequencies, thereby giving an MR image its spatial resolution. An RF transmitter coil 114 surrounds the imaging region 116 and the region of interest 118.

The RF transmitter coil 114 emits RF energy in the form of a magnetic field into the imaging region 116, including into the region of interest 118.

The RF transmitter coil 114 can also receive MR response signals emitted from the region of interest 118. The MR response signals are amplified, conditioned and digitized into raw data using an image-processing system 200, as is known by those of ordinary skill in the art. The image-processing system 200 further processes the raw data using known computational methods, including fast Fourier transform (FFT), into an array of image data. The image data may then be displayed on a monitor 202, such as a computer CRT, LCD display or other suitable display.

The medical device 103 may also be placed within the imaging region 116 of the MRI machine 102. In the example shown in FIG. 1, the medical device 103 may be an ultrasonic ablation instrument used for ablating tissue such as fibroids or cancerous (or non-cancerous) tissue, for breaking up occlusion within vessels, or for performing other treatment of tissues on or within the patient 110. In fact, the medical device 103 can be any type of medical instrument including, without limitation, a needle, catheter, guidewire, radiation transmitter, endoscope, laparoscope, or other instrument. In addition, the medical device 103 can be configured either for placement outside the patient 110 or for insertion into the patient body.

Figure 2:
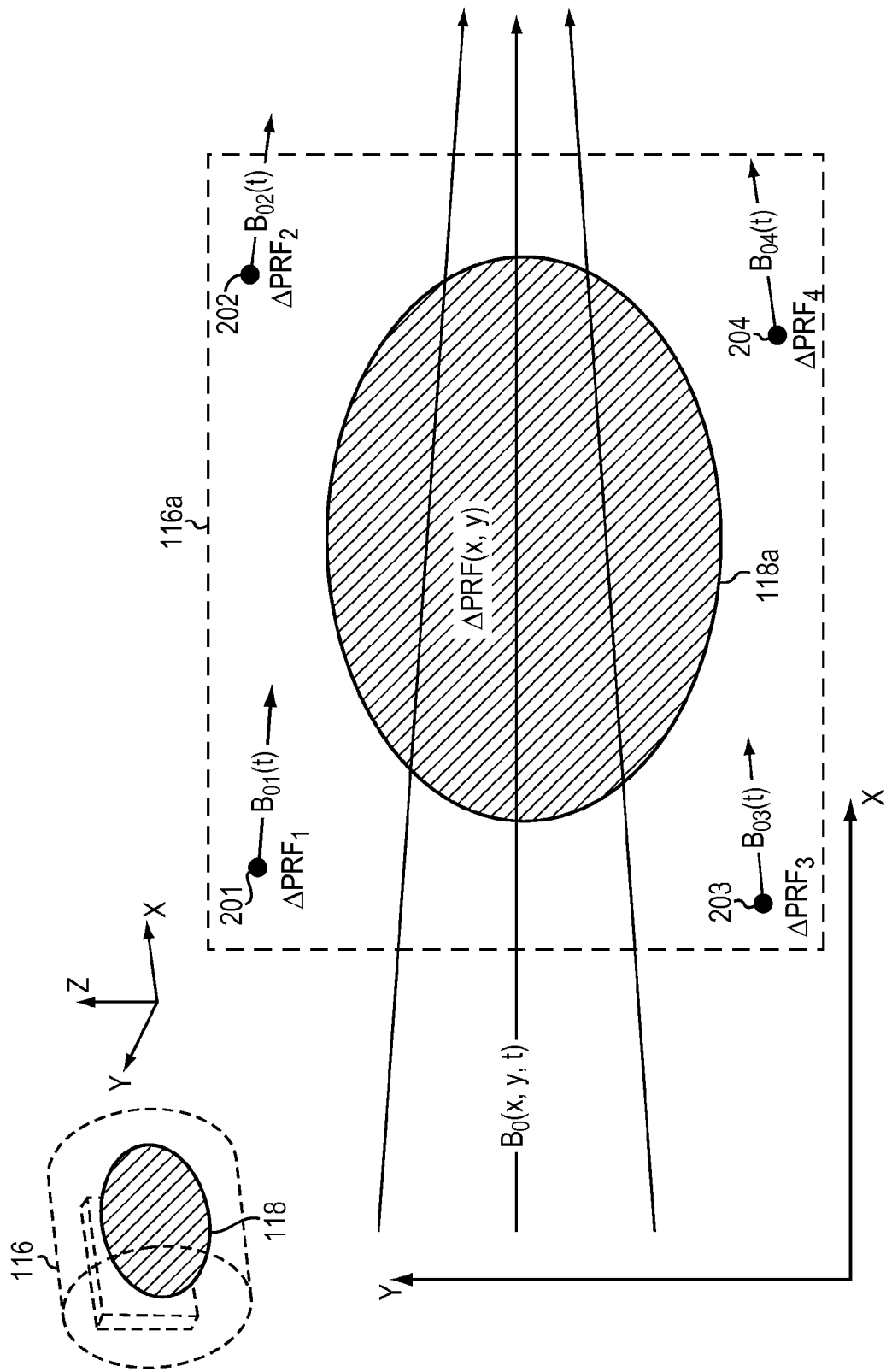
FIG. 2 shows an MR imaging area and illustrates an exemplary method of correcting phase shifts in accordance with an embodiment of the present invention.

A slice of the imaging region 116 (including the region of interest 118) is enlarged in FIG. 2, to illustrate an exemplary method of correcting phase shifts in accordance with an embodiment of the present invention. The illustrated slice of the imaging region 116 includes an MR imaging area 116a within a scan plane of the MRI machine 102 which may be parallel to the X-Y plane. The MR imaging area 116a encompasses and is preferably centered on an area of interest 118a, which may include or be part of a treatment area on or inside the body of a patient 110.

During MR thermal imaging (or any medical procedure involving MR temperature mapping) of the area of interest 118a, a background magnetic field $B_0(x, y, t)$ and the magnetic field gradient may change due to various factors unrelated to changes in temperature. As a result, an initial baseline phase image acquired prior to the change in the background magnetic field becomes unreliable. To solve this problem and also to facilitate measurement of absolute temperatures, a known temperature distribution (e.g., a uniform temperature) may be established initially in the MR imaging area 116a, whereupon a baseline phase image of the imaging area 116a is acquired. At a later time (e.g., before or during a thermal treatment), a second phase image of the imaging area 116a may be acquired. From the second phase image, phase shift corrections and/or temperature corrections may be determined for certain locations or portions of the imaging area 116a that have experienced a known or clinically insignificant change in temperature since the acquisition of the baseline phase image, wherein "a clinically insignificant change" means a sufficiently small change, e.g., on the order of 1-2 degrees Celsius, as to be equivalent for treatment purposes—i.e., within a margin of error that will not produce an adverse physiological effect. For example, temperatures at locations 201, 202, 203, and 204, as shown in FIG. 2, may have held constant because they are relatively far away from the area of interest 118a (or portions thereof), which has received thermal treatment(s). Therefore, the phase changes $\Delta PRF_1$, $\Delta PRF_2$, $\Delta PRF_3$, and $\Delta PRF_4$, detected at the locations 201, 202, 203, and 204, respectively, represent phase shifts arising from non-temperature-related factors such as drifts of local magnetic fields $B_{01}(t)$, $B_{02}(t)$, $B_{03}(t)$, and $B_{04}(t)$ at those respective locations. These phase shifts $\Delta PRF_1$, $\Delta PRF_2$, ΔPRF$_3$, and ΔPRF$_4$ may be extrapolated to help estimate non-temperature-related phase changes in other portions of the imaging area 116a such as in the area of interest 118a. Then, based on the known initial temperature distribution and differences between the second phase image and the baseline phase image, one or more absolute temperatures can be calculated for the area of interest 118a. The temperature calculation may be corrected with the estimated (extrapolated) phase shifts, for example, by applying the estimated phase shifts to the baseline phase image, the second phase image, the differences between the two phase images, or the corresponding temperature differences.

Figure 3:
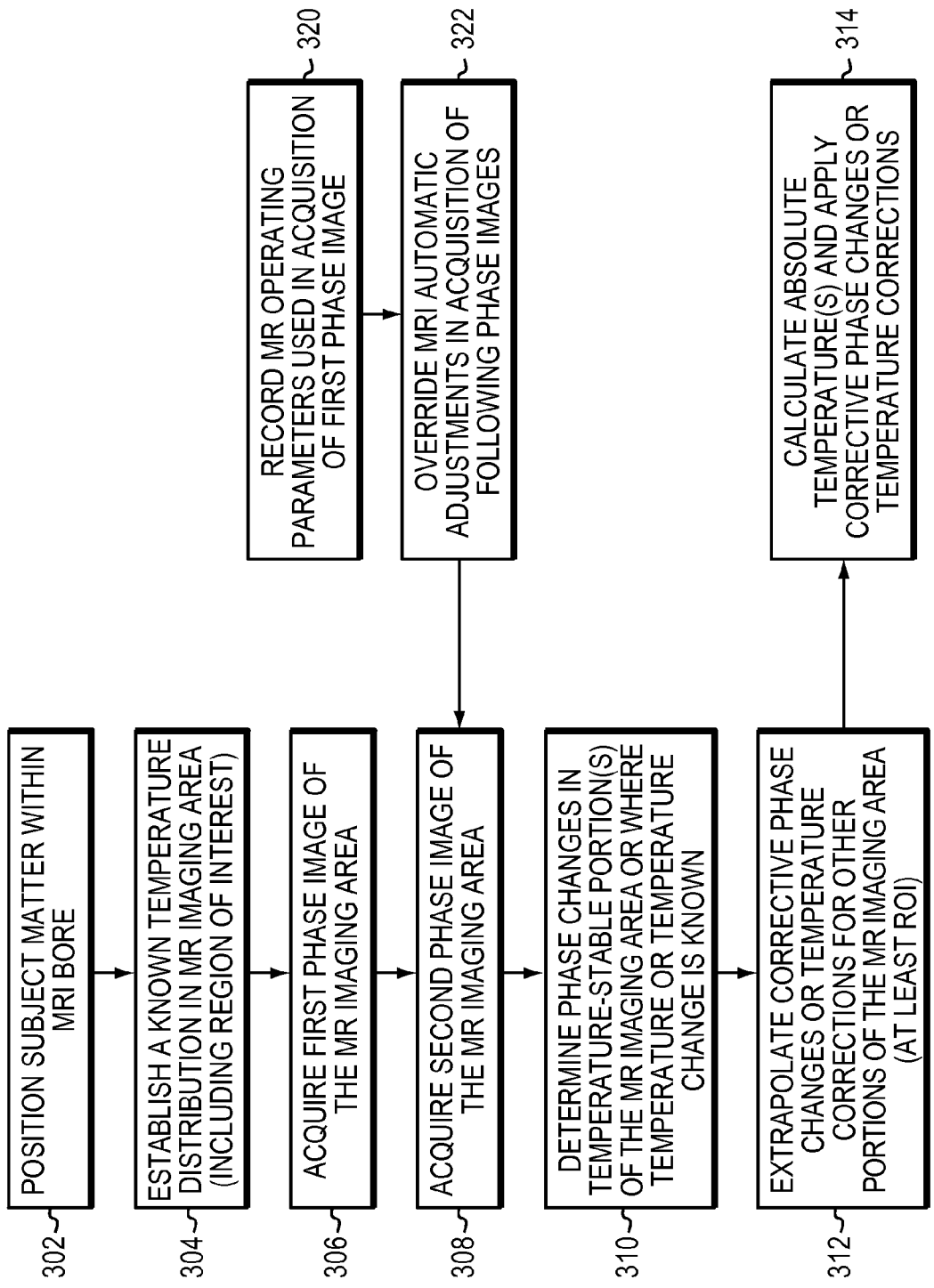
FIG. 3 shows a flow chart illustrating an exemplary method for temperature measurement and phase shift corrections in MR thermometry in accordance with an embodiment of the present invention.

FIG. 3 shows a flow chart illustrating an exemplary method for temperature measurement and phase shift corrections in MR thermometry in accordance with an embodiment of the present invention.

In step 302, a subject such as a human body is positioned within a bore of an MRI machine. A region of interest (ROI) in the subject matter may be identified for purposes of MR temperature measurement, that is, MR thermal imaging or temperature mapping. For example, the region of interest may be a portion of a human body, such as the head region (118) as shown in FIG. 1. In an MR-guided medical procedure, the region of interest may be or include a particular portion of a human body upon which the procedure is performed. For instance, in an MRgFUS procedure, the region of interest may include a general tissue area (e.g., prostate gland or uterine muscles) into which ultrasonic energy is to be focused. The region of interest is typically positioned in or near the center of an imaging area of the MRI machine.

In step 304, a known temperature distribution is established in the MR imaging area including the region of interest. While it is not required or necessary, the temperature distribution may preferably be a uniform one, that is, with one known temperature value across the entire MR imaging area. According to embodiments of the present invention, the known temperature distribution may be achieved through natural and/or artificial processes. For example, a patient's body (including a treatment area) may be allowed to reach a natural equilibrium over an extended period of time, such that the temperature distribution reflects the patient's own body temperature within a small range of tolerance. Alternatively, the treatment area may be actively heated or cooled to reach a desired temperature or temperature distribution.

Figure 4:
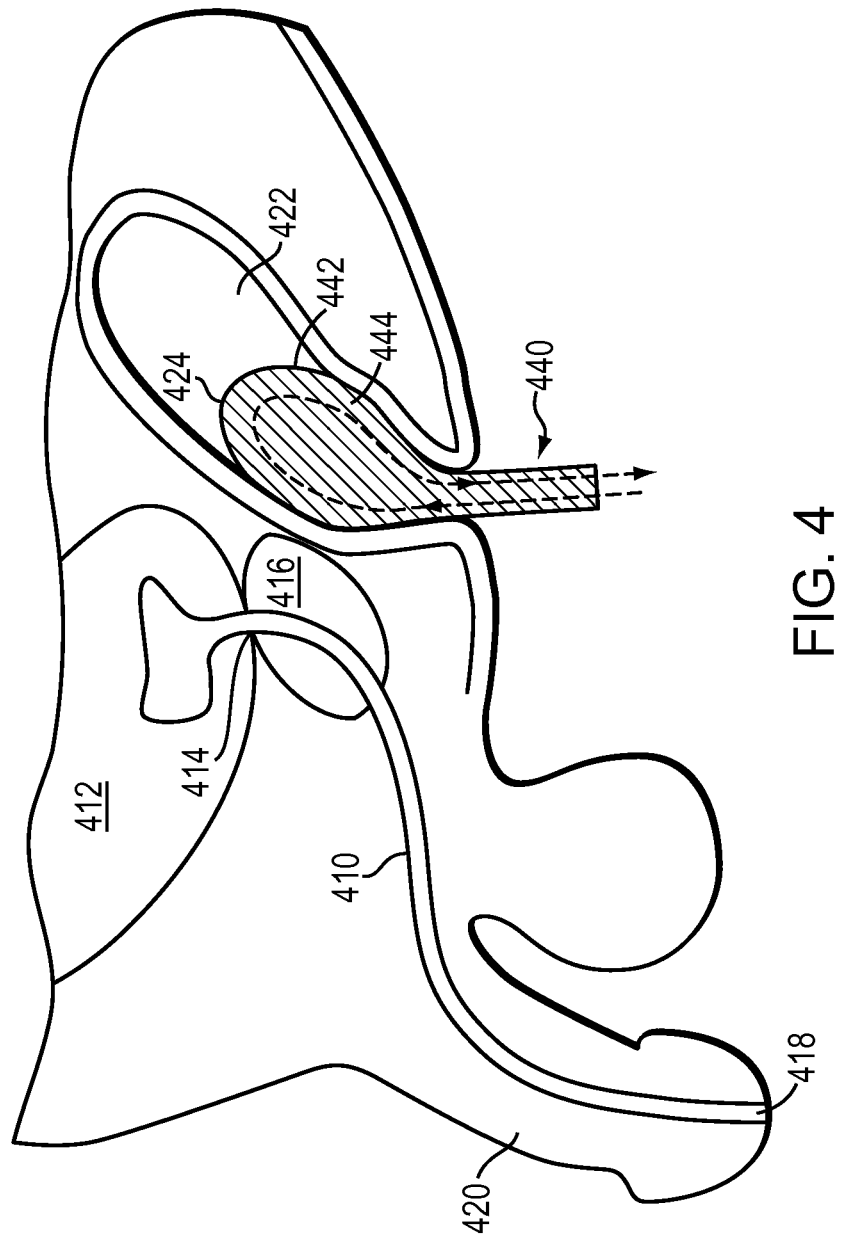
FIG. 4 shows the anatomical structure of a male pelvic region and illustrates an exemplary method of establishing a uniform temperature distribution in accordance with an embodiment of the present invention.

FIG. 4 shows the anatomical structure of a male pelvic region and illustrates an exemplary method of establishing a uniform temperature distribution in accordance with an embodiment of the present invention. There is shown a patient's prostate 416 and its relative location with respect to the urethra 410 and the rectum 422. The urethra 410 is a duct leading from bladder 412, out via an opening 414, through the prostate 416, and out an orifice 418 at the end of penis 420. Growth of the prostate 416 typically results in application of pressure or constriction around the urethra 410, which can interrupt flow of urine from the bladder 412 and through the prostate 416. The prostate 416 is located adjacent to the rectum 422.

According to an embodiment of the present invention, a temperature-regulating device 440 may be employed to establish a desired temperature distribution in a vicinity of the prostate 416. The temperature-regulating device 440 may comprise a balloon 442 that can be inserted into the rectum 422 and positioned against at least a rectal wall adjacent to the prostrate 416. Water 444 (or other liquid coolant) may be circulated through the balloon 442, inflating it to press against the rectal wall. The water 444 may have been heated to a known temperature (e.g., the patient's body temperature) such that a treatment area in and near the prostate 416 may be brought uniformly to that known temperature. The temperature-regulating device 440 may further comprise a transrectal temperature probe (not shown) to monitor temperature(s) in or near the treatment area.

Referring back to FIG. 3, in step 306, a first phase image of the MR imaging area is acquired, preferably soon after the known temperature distribution is established in step 304 above. This first phase image essentially captures a distribution of proton-resonance frequencies in the MR imaging area and serves as a baseline reference for subsequent PRF-shift-based MR temperature measurements. This first phase image is also associated with the known temperature distribution in the MR imaging area, thereby providing a baseline for measuring absolute temperatures.

Then, in step 308, a second phase image of the MR imaging area is acquired. This acquisition step, together with the prior acquisition step 306, may be part of an MR thermal imaging process. The second phase image essentially captures the distribution of proton-resonance frequencies in the MR imaging area at the time of the acquisition step 308. Depending on whether temperature has changed in the imaging area since the baseline reference was acquired in step 306, the second phase image may or may not be substantially different from the first phase image. The second phase image probably includes phase shifts unrelated to temperature changes.

Next, in step 310, phase changes in one or more temperature-stable portions of the MR imaging area are determined based on the second phase image. Certain portions of the imaging area, such as those relatively far away from the thermally treated area of interest, may have experienced little or no temperature change since the acquisition of the first phase image. That is, those temperature-stable portions of the imaging area have substantially retained their temperature levels as reflected in the initial temperature distribution. Therefore, the phase changes detected in the temperature-stable areas arise from factors unrelated to temperature changes. According to an alternative embodiment of the present invention, the non-temperature-related phase changes may be determined from one or more portions of the imaging area where the temperatures at the time of the second phase image are known (e.g., because these portions are subjected to a temperature-regulating device). In that case, the temperature-related part of the total phase changes detected may be removed based on the known temperature changes, leaving only the non-temperature-related phase changes.

The non-temperature-related phase changes (or phase shifts), determined in step 310 for certain portions of the imaging area, may then be extrapolated in step 312 to estimate phase shifts and/or temperature corrections in the rest of the imaging area, including at least the region of interest or a treatment area. Since the phase shifts across the imaging area presumably arise from some common factors, such as drifts in a main magnetic field or gradient fields, the magnitudes of the phase shifts at different locations in the imaging area are related to one another. This allows a distribution of the phase shifts and/or temperature changes in some or all of the imaging area to be mathematically fitted based on the phase shift values of just a few locations. According to one embodiment of the present invention, phase shifts and/or temperature changes in other portions of the imaging area may be extrapolated from a handful of local values based on a two-dimensional (2-D) polynomial fit. For example, phase shifts caused by magnetic field gradient drifts may be fitted with a linear equation, such as:

$$Fit = Ax + By + C$$

where x and y denote the coordinates of each pixel and A, B and C are constants.

In step 314, one or more absolute temperatures in the area of interest may be calculated, and the corrective (non-temperature-related) phase changes determined in step 312 can be applied to or in the temperature calculation, or, alternatively, the temperature corrections determined in step 312 may be applied to the temperature map. Since the initial temperature distribution in the imaging area is known and temperature changes can be calculated from differences between the first and second phase images, absolute temperatures at the time of the second phase image may be determined for at least the area of interest. Of course, the phase differences between the first and second phase images might include non-temperature-related phase shifts. Such phase shifts can be corrected or compensated for, as their values or spatial distribution has already been estimated in step 312 above. As can be appreciated by those skilled in the art, the phase shift values or distribution may be applied to the baseline phase image, the second phase image, the differences between these two phase images, or the calculated temperature change(s) or absolute temperature value(s). For example, the phase shift distribution may be either added to the baseline phase image or subtracted from the second phase image to achieve essentially the same corrective effect on the temperature measurement.

Besides the inherent instabilities of magnetic fields mentioned above, some operating parameters, such as central frequency, gains, and shimming values, are continuously adjusted during normal operation of an MRI system, which may cause further changes in the magnetic fields. As shown in step 320, to account for these adjustments, the operating parameters of the first phase image may be recorded, and then applied to the acquisition of subsequent phase images by overriding MRI automatic adjustments (step 322).

Figure 5:
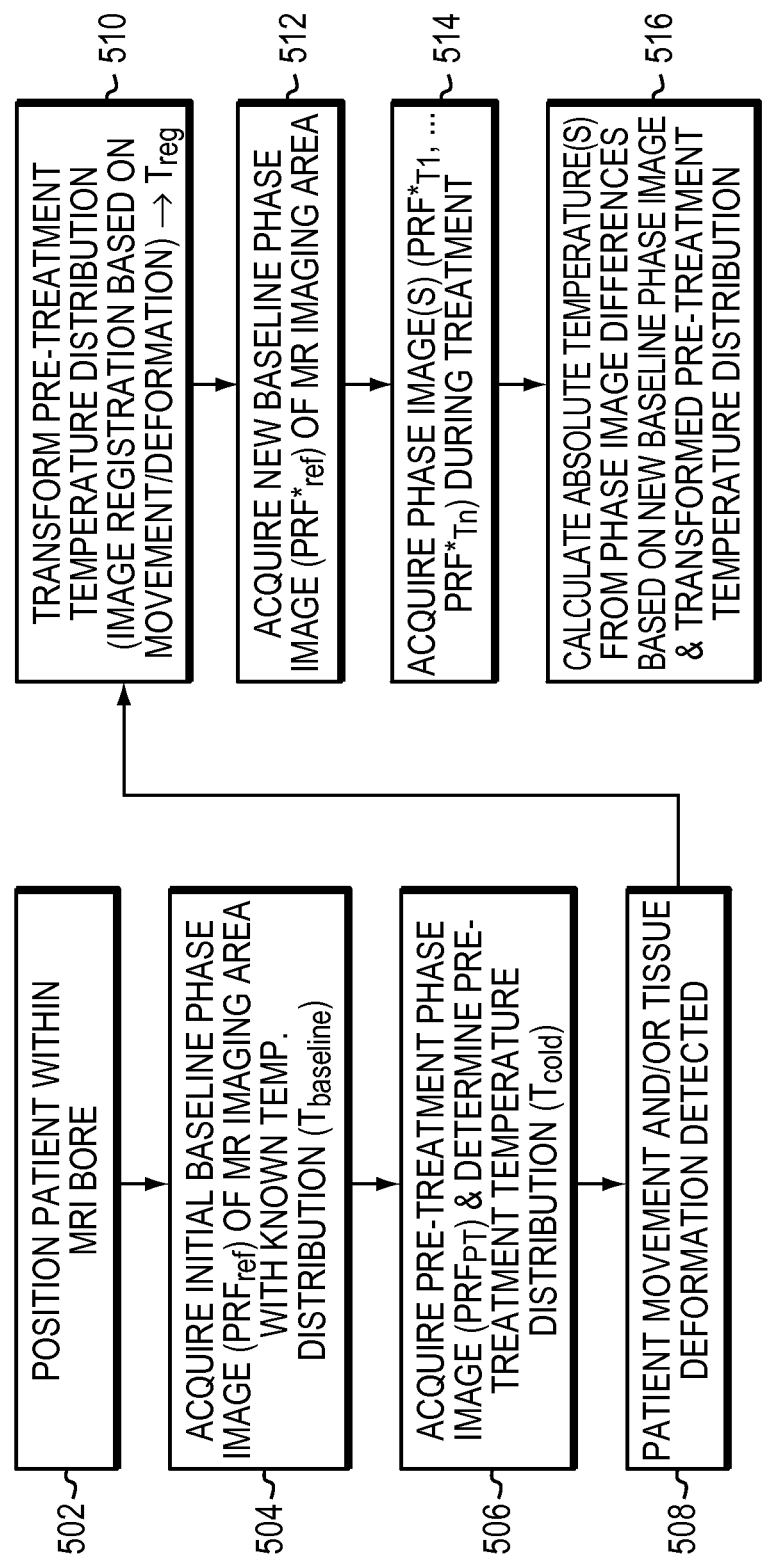
FIG. 5 shows a flow chart illustrating an exemplary method for temperature measurement and movement correction in MR thermometry in accordance with an embodiment of the present invention.

FIG. 5 shows a flow chart illustrating an exemplary method for temperature measurement and movement correction in MR thermometry in accordance with an embodiment of the present invention. The exemplary method again starts by positioning a patient within an MRI bore in step 502.

In step 504, an initial baseline phase image is acquired by scanning an MR imaging area with a known temperature distribution. The baseline phase image may be denoted $PRF_{ref}$, and the known temperature distribution may be denoted $T_{baseline}$.

Then, in step 506 (prior to a thermal treatment, for example), a pre-treatment phase image (denoted $PRF_{PT}$) is acquired, and a pre-treatment temperature distribution (denoted $T_{cold}$) is determined based on the known temperature distribution $T_{baseline}$ and differences between the pre-treatment phase image and the baseline phase image, i.e., $\Delta PRF_{correc} = PRF_{PT} - PRF_{ref}$. Thus, the pre-treatment temperature distribution is $T_{cold} = T_{baseline} + \Delta T_{correc}$, wherein $\Delta T_{correc}$ represents the temperature difference corresponding to the phase difference $\Delta PRF_{correc}$. The calculation of the pre-treatment temperatures here may certainly benefit from the phase shift corrections described above, as can be appreciated by those skilled in the art.

Normally, once the pre-treatment temperature distribution is determined, the treatment may begin, and additional phase images may be repeatedly acquired for temperature measurement during the treatment. Subsequent temperature measurements will generally rely on the baseline phase image and the known temperature distribution. However, as shown in step 508, a patient movement and/or tissue deformation may be detected, which alters the post-movement phase image and makes the baseline phase image irrelevant as it no longer reflects an accurate position and/or shape of the treatment area and may cause thermal artifacts. This problem may be addressed as follows.

In step 510, the pre-treatment temperature distribution $T_{cold}$ is transformed to reflect the new position and/or shape of the treatment area through image registration based on the detected movement and/or deformation. The resulting, transformed temperature distribution may be denoted $T_{reg}$.

Figure 6:
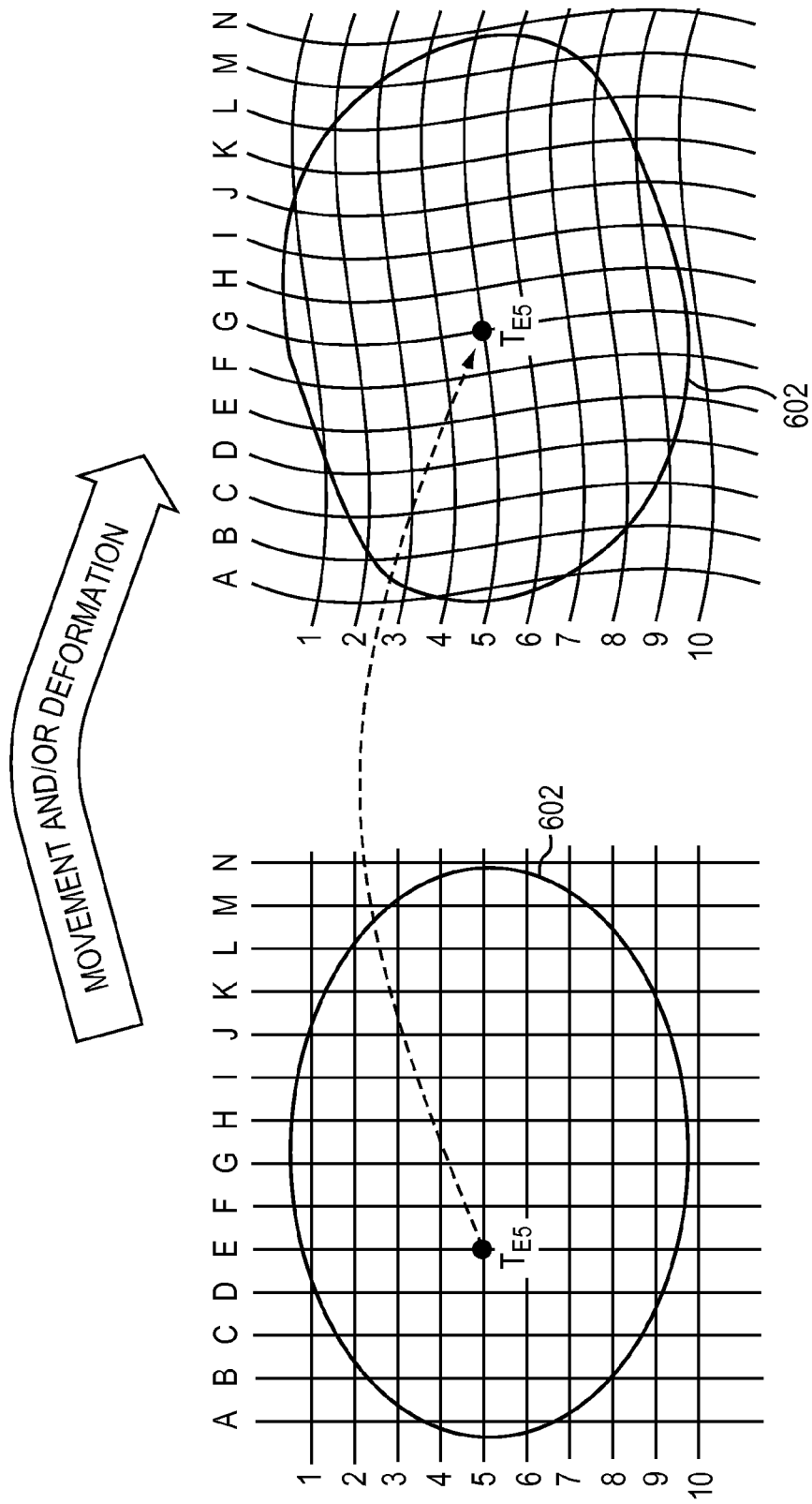
FIG. 6 illustrates an exemplary method of image registration for movement and/or deformation correction in accordance with an embodiment of the present invention.

FIG. 6 illustrates an exemplary method of image registration for movement and/or deformation correction in accordance with an embodiment of the present invention. FIG. 6 shows an originally oval-shaped object 602 (on the left) that becomes deformed into a different shape (on the right). The original object 602 may have a first coordinate system associated with it. The first coordinate system may include horizontal and vertical straight lines that define a rectangular grid. The deformed object 602, on the other hand, may have a second coordinate system associated with it. The second coordinate system may include curved lines defining a somewhat warped grid. In MR thermometry, the object 602 may represent an organ or a tissue area that becomes mechanically deformed without any substantial change in temperature. If the object 602 has a known temperature distribution right before the deformation, a goal of image registration is to establish a transformed temperature distribution wherein the temperature value at each pixel location can be related back to a corresponding pre-deformation value even though the pixel may have shifted in the temperature map. For example, in FIG. 6, a pixel falling on the intersection of the grid lines E and 5 may have an original temperature ($T_{E5}$) prior to the deformation of the object 602. Assuming no temperature change accompanies the deformation, the same pixel location will retain the same temperature ($T_{E5}$) in the deformed object 602. Many image registration methods may be used in accordance with the present invention. According to one embodiment, image registration may be accomplished using the well-known Demons algorithm.

Referring again to FIG. 5, in step 512, a new baseline phase image (denoted $PRF^*_{ref}$) is acquired by scanning the MR imaging area. The new baseline phase image reflects the position and shape of the area of interest (e.g., the treatment area) after the movement and/or deformation detected in step 508.

Next, in step 514, one or more additional phase images (e.g., $PRF^*_{T1}, \ldots, PRF^*_{Tn}$) of the MR imaging area are acquired during treatment for temperature measurement and monitoring purposes.

With each of the additional phase image(s), relative and/or absolute temperature(s) may be calculated, in step 516, based on phase image differences as compared to the new baseline image $PRF^*_{ref}$ and further based on the transformed pre-treatment temperature distribution $T_{reg}$. For example, if $\Delta PRF_{rel}$ denotes image differences between a k-th phase image $PRF^*_{Tk}$ and the new baseline image $PRF^*_{ref}$—

$$\Delta PRF_{rel} = PRF^*_{Tk} - PRF^*_{ref}$$

which translates to a temperature increment of $\Delta T_{rel}$, then the temperature distribution at the time of the k-th phase image is $$T_k = T_{reg} + \Delta T_{rel}.$$

Figure 7:
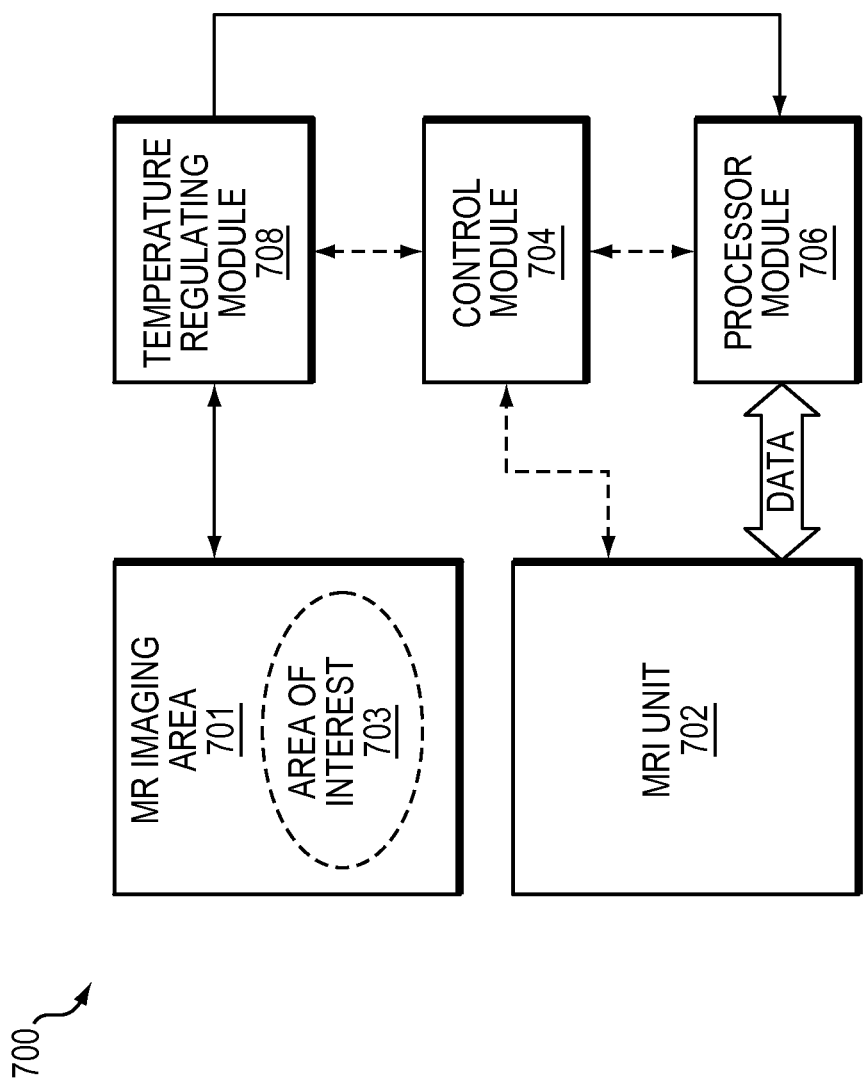
FIG. 7 shows a block diagram illustrating an exemplary system for temperature measurement and corrections in MR thermometry in accordance with an embodiment of the present invention.

FIG. 7 shows a block diagram illustrating an exemplary system 700 for temperature measurement and corrections in MR thermometry in accordance with an embodiment of the present invention. The system 700 comprises an MRI unit 702 whose imaging area 701 covers an area of interest 703. The MRI unit 702 may be configured for thermal imaging of the imaging area 701 and/or the area of interest 703 based on the PRF shift method. A control module 704 in communication with the MRI unit 702 coordinates phase image acquisitions by the MRI unit 702. The system 700 may also comprise a temperature-regulating module 708 including heating/cooling devices and thermal sensors, which may be directed by the control module 704 to establish and monitor a desired temperature distribution in the MR imaging area 701. The image acquisition data from the MRI unit 702, as well as temperature data from the temperature-regulating module 708, may be processed by a processor module 706 to implement the above-described techniques of temperature measurement and phase shift corrections in thermal imaging of the area of interest 703.

For example, according to one embodiment of the present invention, the control module 704 may cause the temperature-regulating module 708 to establish a uniform temperature in the MR imaging area 701. The control module 704 may also cause the MRI unit 702 to acquire a first phase image of the MR imaging area 701 with the uniform temperature distribution, and the first phase image can serve as an initial baseline reference. Next, the control module 704 may cause the MRI unit 702 to acquire a second phase image of the MR imaging area. Then, the processor module 706 may determine, from the second phase image, a first set of phase changes in one or more portions of the MR imaging area 701 that have experienced little change in temperature since the acquisition of the first phase image; that is, the first set of phase changes will reflect non-temperature-related phase shifts. The processor module 706 may further determine a second set of phase changes (or a distribution of phase shifts) in at least the area of interest 703 by extrapolating the first set of phase changes. Finally, the processor module 706 may calculate a distribution of absolute temperatures in the area of interest 703 based on the known initial temperature distribution and a difference between the second phase image and the first phase image, and the temperature calculation can be corrected based on the second set of phase changes.

It should be noted that, although portions of the system 700 have been illustrated as discrete components in FIG. 7, some of these components (e.g., control module 704, processor module 706, and the temperature-regulating module 708) may be combined with one another and/or implemented as integral part(s) of the MRI unit 702. Other variations exist for configuring the system 700 as can be appreciated by those skilled in the art.

While the foregoing description includes many details and specificities, it is to be understood that these have been included for purposes of explanation only, and are not to be interpreted as limitations of the present invention. It will be apparent to those skilled in the art that other modifications to the embodiments described above can be made without departing from the spirit and scope of the invention. Accordingly, such modifications are considered within the scope of the invention as intended to be encompassed by the following claims and their legal equivalents.

What is claimed is:

1. A method of performing proton resonance frequency (PRF) based magnetic resonance (MR) temperature measurement, the method comprising the steps of:
    using an MRI unit, acquiring a first phase image of an MR imaging area having a known temperature distribution, the MR imaging area comprising an area of interest;
    using the MRI unit, acquiring a second phase image of the MR imaging area subsequent to the acquisition of the first phase image;
    without modifying the first image, determining, from differences between the second phase image and the first phase image, one or more first corrections in one or more portions of the MR imaging area that have experienced a known or clinically insignificant change in temperature since the acquisition of the first phase image;
    determining one or more second corrections in at least the area of interest by extrapolating the one or more first corrections;
    assigning a first set of one or more absolute temperatures to the area of interest based at least in part on (i) the known temperature distribution and (ii) the one or more second corrections,
    detecting a movement and/or deformation of the area of interest;
    determining a new temperature distribution of at least the area of interest by registering the known temperature distribution to the new temperature distribution based at least in part on the detected movement and/or deformation;
    acquiring a third phase image of the MR imaging area subsequent to the detected movement and/or deformation;
    acquiring a fourth phase image of the MR imaging area subsequent to the acquisition of the third phase image; and
    assigning a second set of one or more absolute temperatures to the area of interest based at least in part on (i) the new temperature distribution and (ii) a difference between the fourth phase image and the third phase image.

2. The method of claim 1, further comprising:
    establishing the known temperature distribution in the MR imaging area.

3. The method of claim 2, further comprising:
    establishing a uniform temperature in the MR imaging area.

4. The method of claim 1, wherein the MR imaging area is centered on the area of interest.

5. The method of claim 1, wherein (i) the area of interest comprises a treatment area of a patient undergoing an MR-guided focused ultrasound treatment, and (ii) the MR imaging area comprises at least a portion of the patient's body.

6. The method of claim 5, wherein the treatment area comprises the patient's prostate area.

7. The method of claim 6, further comprising:
    establishing a uniform temperature in the MR imaging area by circulating heated water in a balloon pressed against the patient's rectal wall.

8. The method of claim 7, wherein the uniform temperature is substantially the same as the patient's body temperature.

9. The method of claim 1, further comprising:
    determining the second correction(s) with a two-dimensional (2-D) polynomial fit based on the first correction(s).

10. The method of claim 9, wherein the two-dimensional (2-D) polynomial fit is a linear fit.

11. The method of claim 1, further comprising:
    recording MR operating parameters used in the acquisition of the first phase image; and
    overriding MRI automatic adjustments in the acquisition of the second phase image with the recorded MR operating parameters.

12. The method of claim 1, wherein registering the known temperature distribution to the new temperature distribution comprises transformation of a temperature value at each pixel location in the new temperature distribution to a corresponding pre-movement and/or pre-deformation value in the known temperature distribution.

13. A system for performing proton resonance frequency (PRF) based magnetic resonance (MR) temperature measurement, the system comprising:
   an MRI unit;
   a controlling means for communicating with the MRI unit, and causing the MRI unit to:
      acquire a first phase image of an MR imaging area having a known temperature distribution, the MR imaging area comprising an area of interest, and
      acquire a second phase image of the MR imaging area subsequent to the acquisition of the first phase image; and
   a processing means for accessing to image data acquired by the MRI unit, and:
      determining, from differences between the second phase image and the first phase image without modifying the first image, one or more first corrections in one or more portions of the MR imaging area that have experienced a known or clinically insignificant change in temperature since the acquisition of the first phase image,
      determining one or more second corrections in at least the area of interest by extrapolating the one or more first corrections,
      assigning a first set of one or more absolute temperatures to the area of interest based at least in part on (i) the known temperature distribution and (ii) the one or more second corrections,
      detecting a movement and/or deformation of the area of interest;
      determining a new temperature distribution of at least the area of interest by registering the known temperature distribution to the new temperature distribution based at least in part on the detected movement and/or deformation;
      acquiring a third phase image of the MR imaging area subsequent to the detected movement and/or deformation;
      acquiring a fourth phase image of the MR imaging area subsequent to the acquisition of the third phase image; and
      assigning a second set of one or more absolute temperatures to the area of interest based at least in part on (i) the new temperature distribution and (ii) a difference between the fourth phase image and the third phase image.

14. The system of claim 13, further comprising:
   a temperature regulating means for establishing the known temperature distribution in the MR imaging area.

15. The system of claim 14, wherein the temperature regulating means further establishes a uniform temperature in the MR imaging area.

16. The system of claim 14, wherein the temperature regulating means comprises a balloon, adapted to be pressed against a patient's rectal wall, through which heated water is circulated, thereby establishing a uniform temperature in the MR imaging area.

17. The system of claim 16, wherein the uniform temperature is substantially the same as the patient's body temperature.

18. The system of claim 13, wherein the processing means is further configured to:
   determine the one or more second corrections with a two-dimensional (2-D) polynomial fit based on the one or more first corrections.

19. The system of claim 18, wherein the two-dimensional (2-D) polynomial fit is a linear fit.

20. The system of claim 13, wherein the controlling means is further configured to:
   record MR operating parameters used by the MRI unit in the acquisition of the first phase image; and
   override automatic adjustments of the MRI unit with the recorded MR operating parameters during the acquisition of the second phase image.

21. A non-transitory computer-readable medium storing computer-executable codes for causing at least one processor to correct proton resonance frequency (PRF) based magnetic resonance (MR) temperature measurement, the computer-readable medium comprising:
   computer-executable code adapted to acquire a first phase image of an MR imaging area having a known temperature distribution, the MR imaging area comprising an area of interest;
   computer-executable code adapted to acquire a second phase image of the MR imaging area subsequent to the acquisition of the first phase image;
   computer-executable code adapted to determine, from differences between the second phase image and the first phase image without modifying the first image, one or more first corrections in one or more portions of the MR imaging area that have experienced a known or clinically insignificant change in temperature since the acquisition of the first phase image;
   computer-executable code adapted to determine one or more second corrections in at least the area of interest by extrapolating the one or more first corrections;
   computer-executable code adapted to assign a first set of one or more absolute temperatures to the area of interest based at least in part on (i) the known temperature distribution and (ii) the one or more second corrections,
   computer-executable code adapted to detect a movement and/or deformation of the area of interest:
   computer-executable code adapted to determine a new temperature distribution of at least the area of interest by registering the known temperature distribution to the new temperature distribution based at least in part on the detected movement and/or deformation;
   computer-executable code adapted to acquire a third phase image of the MR imaging area subsequent to the detected movement and/or deformation;
   computer-executable code adapted to acquire a fourth phase image of the MR imaging area subsequent to the acquisition of the third phase image; and
   computer-executable code adapted to assign a second set of one or more absolute temperatures to the area of interest based at least in part on (i) the new temperature distribution and (ii) a difference between the fourth phase image and the third phase image.

22. The computer-readable medium of claim 21, further comprising:
   computer-executable code adapted to determine the one or more second corrections with a two-dimensional (2-D) polynomial fit based on the one or more first corrections.

23. The computer-readable medium of claim 22, wherein the two-dimensional (2-D) polynomial fit is a linear fit.

24. The computer-readable medium of claim 21, further comprising:
   computer-executable code adapted to record MR operating parameters used in the acquisition of the first phase image; and
   computer-executable code adapted to override MRI automatic adjustments in the acquisition of the second phase image with the recorded MR operating parameters.

* * * * *